US006706153B2

United States Patent
Frentzen et al.

(10) Patent No.: US 6,706,153 B2
(45) Date of Patent: *Mar. 16, 2004

(54) PROCESS FOR THE SEPARATION OF A KETOXIME OR ALDOXIME FROM AN AMIDE

(75) Inventors: Yvonne H. Frentzen, Venlo (NL); Nicolaas F. Haasen, Limbrichtt (NL); Henricus F. W. Wolters, Echt (NL)

(73) Assignee: DSM N.V., Heerlen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/226,718

(22) Filed: Jan. 7, 1999

(65) Prior Publication Data

US 2002/0005343 A1 Jan. 17, 2002

Related U.S. Application Data

(63) Continuation of application No. PCT/NL97/00395, filed on Jul. 8, 1997.

(30) Foreign Application Priority Data

Jul. 11, 1996 (NL) ............................................. 1003564

(51) Int. Cl.$^7$ ........................ B01D 3/38; C07D 201/16; C07C 251/32
(52) U.S. Cl. ............... 203/2; 203/79; 203/80; 203/29; 540/540; 564/267
(58) Field of Search ................ 203/2, 91–92, 203/28, 29, 95–96, 79–80; 540/540, 492, 485; 564/267

(56) References Cited

U.S. PATENT DOCUMENTS 3,016,376 A * 1/1962 Francis ........................ 549/540
3,248,388 A * 4/1966 Wintersberger et al. .... 549/540
3,288,687 A * 11/1966 Zimmerli et al. ............. 203/35
3,867,373 A * 2/1975 Wagner ........................ 540/492
4,326,925 A   4/1982 Senni et al.
4,349,520 A * 9/1982 Bonfield et al. ............. 423/387
5,227,028 A   7/1993 Bosman et al.
6,261,526 B1 * 7/2001 Virnig et al. ................ 423/139

FOREIGN PATENT DOCUMENTS

| DE | 861 383   |   | 1/1953  |
|----|-----------|---|---------|
| DE | 2641381   | * | 3/1978  |
| EP | 464 943   |   | 1/1992  |
| FR | 1189072   | * | 9/1959  |
| FR | 1337527   | * | 8/1963  |
| FR | 2 450 255 |   | 9/1980  |
| GB | 1 286 427 |   | 8/1972  |
| JP | 56100758  | * | 8/1981  |
| SU | 168705    | * | 9/1965  |
| SU | 186491    | * | 10/1966 |
| SU | 225885    | * | 7/1969  |

OTHER PUBLICATIONS

Goszczynski et al "analysis of a mixture containing .epsilon.– caprolactam", chem. Anal. (Warsaw),3,131–6, 1958.*

Database WPI Section ch, week 8350 derwent Publications Ltd., London GB; AN 83–842561 XP002024708 & SU 225 885 A (Nitrogen Organ Inte), 7 Jul. 11969 see abstract.

* cited by examiner

Primary Examiner—Virginia Manoharan
(74) Attorney, Agent, or Firm—Pillsbury Winthrop LLP

(57) ABSTRACT

The invention relates to a process for the separation of a ketoxime or aldoxime from a ketoxime- or aldoxime-containing amide mixture in which the ketoxime or aldoxime is separated from the amide mixture by distillation. This has proved to be a very simple and direct method for separating the ketoxime and/or aldoxime from the desired amide.

26 Claims, No Drawings

PROCESS FOR THE SEPARATION OF A KETOXIME OR ALDOXIME FROM AN AMIDE

This is a continuation of: International Appln. No. PCT/NL97/00395 filed Jul. 8, 1997 which designated the U.S.

This invention relates to a process for the separation of a ketoxime or aldoxime from a ketoxime- or aldoxime-containing amide mixture, for instance such a mixture obtained from a Beckman rearrangement reaction.

BACKGROUND OF THE INVENTION

Such a process has been disclosed in GB-A-1286427, which describes a process in which an oxime-containing lactam mixture is treated with sulphur dioxide. For this process, at least 1 mol of sulphur dioxide is added per mol of oxime. The excess sulphur dioxide is subsequently removed and, through distillation, of caprolactam the latter is obtained in pure form.

The disadvantage of such a process lies in the introduction of a foreign substance into the process, which must ultimately be removed from the process at a later stage.

Moreover, oximes, such as ketoxime or aldoxime, function as chain terminators in the polymerization of amides, for instance in the polymerization of caprolactam to nylon-6, which is disadvantageous. It is therefore important to seek to obtain the desired amide product in the purest form possible.

GENERAL DESCRIPTION OF THE INVENTION

The object of this invention is to separate the ketoxime or aldoxime from the amide in a simple and direct process technique.

This object is accomplished by this invention by separation of the ketoxime or aldoxime by means of distillation.

This is an extremely surprising result, since GB-A-1286427 states that separation of an oxime from a lactam is either impossible or much too expensive to be realized by means of simple, straightforward physical separation techniques. It is also surprising since the ketoxime or aldoxime is not stable thermally. Undesired by products are exptected to be formed upon distillation, for example octahydrophenaxine (OHP). OHP is disadvantageous to the ultimate quality of the caprolactam.

It is generally known that amides, in particular lactams (for instance, ,-caprolactam), may be produced by means of a Beckmann rearrangement of ketoximes or aldoximes, for instance cyclohexanone oxime. This rearrangement takes place with the aid of a solid acid or neutral catalyst. Such a rearrangement may be conducted in either the gas phase or in the liquid phase.

As examples of a solid acid or neutral catalyst, use may be made of boric acid on a support, such as for instance silica or alumina and crystalline silicas, for instance silicalite I (a silicon-rich MFI) and silicalite II (a silicon-rich MEL); alternatively, an acid ion exchanger or (mixed) metal oxides can be used.

An advantage of this catalysis approach to the process is that no ammonium sulphate is formed as byproduct, as is the typical case in a Beckmann rearrangement through treatment of the ketoxime or aldoxime with the aid of strong acids such as sulfuric acid. The desired amide must then be recovered via neutralization of the reaction mixture, usually by use of ammonia water. However, this gives rise to the formation of a large amount of ammonium sulphate as byproduct.

However, in Beckmann rearrangements conducted in either the liquid phase or in the gas phase, only incomplete conversion of the ketoxime or aldoxime may take place, so that along with the desired amide, a certain amount of unreacted ketoxime or aldoxime leaves the reactor. On the other hand, it is most desirable that the ketoxime or aldoxime be fully removed from the oxime-containing mixture in view of disruptions in the further downstream processing of the amide. Therefore, it is of importance to obtain a high purity of the desired amide.

Examples of ketoximes or aldoximes in ketoxime- or aldoxime-containing amide mixtures that can be obtained from a Beckmann rearrangement include unsaturated and saturated, substituted or unsubstituted aliphatic ketoximes or aldoximes or cyclic ketoximes with 2–12 carbon atoms, for instance acetone oxime, acetaldoxime, benzaldoxime, propanaldoxime, butanaldoxime, butanone oxime, 1-butene oxime, cyclopropanone oxime, cyclohexanone oxime, cyclooctanone oxime, cyclododecanone oxime, cyclopentenone oxime, cyclododecenone oxime, 2-phenyl cyclohexanone oxime, cyclohexenone oxime.

The distillation techniques employed in the practice of this invention include both steam distillation and distillation under reduced pressure. The temperature at which the distillation can be effected is between 80° C. and 180° C. Preferably, the temperature is between 100° C. and 160° C.

The distillate containing the ketoxime or aldoxime can then be returned to the reactor for another or continuing rearrangement operation.

The distillation can be carried out in two stages, which stages may in turn be subdivided into theoretical trays, the pressure drop being less than 200 Pa per theoretical tray. Said pressure drop of less than 200 Pa relates to a measurement under standard conditions, namely the reaction of a cis-trans decalin mixture (50% cis and 50% trans) under total reflux at a pressure of 50 mbar and a vapour rate of 5.2 m/s.

In the distillation according to the invention various evaporators can be used, for instance a falling-film evaporator. As packing material for the distillation column any packing is suitable which gives a pressure drop of less than 200 Pa per theoretical tray. Such a packing materials are generally commercially available, for instance Intalox$^R$ metal packing (described in Chemical Engineering Progress, March 1979, pp. 86–91), Sulzer BX$^R$ (see Chemie Ingenieur Technik, volume 37, page 322, 1965) and Sulzer Mellapak$^R$ (see Chemical Engineering Progress, November 1977, pp. 71–77). Preferably, a packing material is used with which the said pressure drop is less than 100 Pa per theoretical tray, for instance the above-mentioned Mellapak$^R$ of Sulzer. The required number of theoretical trays in the rectification column is usually from 1–15, preferably between 5–12, and more preferably between 8–12. The caprolactam-oxime mixture to be purified can be fed to the top of the column or to the column itself. As a rule, a reflux ratio between 3 and 8 is used. The purity of the bottom product obtained according to the invention is usually >99%.

The rectification column is preferably operated at a bottom pressure of 500–3000 Pa and preferably at a bottom temperature of between 120 and 160° C.

EXAMPLES OF THE INVENTION

The invention will now be elucidated with reference to certain exemplary embodiments, without however being limited thereto.

Example I

A mixture consisting of 700 g of water, 4.57 g of cyclohexanone oxime and 16 g of caprolactam was supplied to a 1-liter vessel. The vessel temperature was raised to 100° C., after which steam was passed through the mixture. Gaseous stream was cooled and in total, six distillate fractions were collected. In each fraction and in each sample of the residue, taken at the same points of time, the cyclohexanone oxime content and the caprolactam content were determined by means of gas chromatography in an HP gas chromatograph with a CP wax 52 CB column. Detection took place with the aid of an FID detector. The results are presented in Table I.

TABLE I

| fraction + cumulative weight | oxime in distillate, cumulative in g | oxime in residue, in g | lactam in distillate, cumulative in g | lactam in residue, in g |
|---|---|---|---|---|
| fraction 1 28.7 g | 0.53 | 4.04 | 0.0035 | 16.10 |
| fraction 2 175 g | 1.95 | 2.62 | 0.029 | 15.93 |
| fraction 3 265 g | 3.03 | 1.53 | 0.08 | 15.86 |
| fraction 4 420 g | 3.90 | 0.66 | 0.15 | 15.82 |
| fraction 5 950 g | 4.52 | 0.05 | 1.54 | 14.31 |
| fraction 6 1000 g | 4.57 | 0.003 | 3.3 | 12.67 |

From this table it can be seen that there are minimum losses of lactam in the overhead distillate and substantial recovery of nearly pure lactam in the distillate bottoms, coupled with substantial removal of the undesired oximes.

Example II

A vacuum distillation set-up consisted of a 30 cm column (Widmer$^R$) with 10–15 theoretical trays. The reflux ratio was 5. The reflux ratio is defined as reflux flow relative to product flow. At the top of the column the pressure was 5 mm Hg, at a temperature of 130° C. At the bottom of the column the temperature was 151° C. The composition of the starting material obtained upon the Beckmann rearrangement was as follows:
40 g of caprolactam flakes and 10 g of cyclohexanone oxime, twice recrystallized from toluene, so that >99% pure cyclohexanone oxime was obtained.

This starting material was transferred one time only to the bottom of the column. The distilled fractions obtained as overhead product of the column were gas chromatographically analyzed as described in example I. Upon completion of the distillation the residue obtained from the bottom of the column was also analyzed. The results are presented in Table II. The distilled fractions were returned to the vessel in which the Beckmann rearrangement took place. A large portion of the oxime was found in the piping due to condensation and solidification and as such was not included in the various distillate fractions.

TABLE II

| | % oxime | g of oxime | g of lactam |
|---|---|---|---|
| distillate fraction I 4.01 g | 30.4 | 1.22 | 2.79 |
| distillate fraction 2 2.10 g | 58 | 1.22 | 0.88 |
| distillate | 11.6 | 0.38 | 2.88 |

TABLE II-continued

| | % oxime | g of oxime | g of lactam |
|---|---|---|---|
| fraction 3 3.26 g | | | |
| residue 32 g | — | <100 ppm | 32 |
| remainder in off-gas and piping | 86.4 | 6.91 | 1.09 |

What is claimed is:

1. A process comprising
   distilling a mixture of cyclohexanone oxime and caprolactam at a temperature a range between 80° C. and 180° C., and recovering, as overheads, cyclohexanone oxime from said mixture, and
   preparing caprolactam from the recovered cyclohexanone oxime.

2. Process according to claim 1, wherein the distilling is steam distilling.

3. Process according to claim 1, wherein the distilling is conducted at a temperature between 100° C. and 160° C.

4. Process according to claim 1, wherein the distilling is conducted in two stages.

5. Process according to claim 1, wherein said mixture comprising caprolactam and cyclohexanone oxime is obtained from a Beckman rearrangement reaction.

6. A process comprising
   distilling a mixture of cyclohexanone oxime and caprolactam at a temperature in a range between 80° C. and 180° C., in from 1 to 15 theoretical trays and recovering, as overheads, cyclohexanone oxime from said mixture, and preparing caprolactam from the recovered cyclohexanone oxime.

7. Process according to claim 6, wherein the distilling is conducted in a column with 5 to 15 theoretical ways.

8. Process according to claim 6, wherein the distilling is steam distilling.

9. Process according to claim 6, wherein the distilling is conducted at a temperature between 100° C. and 160° C.

10. Process according to claim 6, wherein the pressure drop per theoretical tray is less than 200 Pa.

11. Process according to claim 6, wherein the distilling is conducted in two stages.

12. Process according to claim 6, wherein said mixture comprising caprolactam and cyclohexanone oxime is obtained from a Beckman rearrangement reaction.

13. Process according to claim 6, wherein the distilling is carried out at a temperature between 100° C. and 160° C., in a distillation column having from 5 to 15 theoretical trays.

14. A process for separating cyclohexanone oxime from a mixture comprising cyclohexanone oxime and caprolactam, said process comprising
   distilling said mixture at a temperature in a range between 80° C. and 180° C., and recovering, as overheads, cyclohexanone oxime from said mixture.

15. Process according to claim 14, wherein the distilling is steam distilling.

16. Process according to claim 14, wherein the distilling is conducted at a temperature between 100° C. and 160° C.

17. Process according to claim 14, wherein the distilling is conducted in two stages.

18. Process according to claim 14, wherein said mixture comprising caprolactam and cyclohexanone oxime is obtained from a Beckman rearrangement reaction.

19. A process for separating cyclohexanone oxime from a mixture comprising cyclohexanone oxime and caprolactam, said process comprising distilling said mixture at a temperature in a range between 80° C. and 180° C., in from 1 to 15 theoretical trays and recovering, as overheads, cyclohexanone oxime from said mixture.

20. Process according to claim 19, wherein the distilling is conducted in a column with 5 to 15 theoretical trays.

21. Process according to claim 19, wherein the distilling is steam distilling.

22. Process according to claim 19, wherein the distilling is conducted at a temperature between 100° C. and 160° C.

23. Process according to claim 19, wherein the distilling is conducted such that the pressure drop per theoretical tray is less than 200 Pa.

24. Process according to claim 19, wherein the distilling is conducted in two stages.

25. Process according to claim 19, wherein said mixture comprising caprolactam and cyclohexanone oxime is obtained from a Beckman rearrangement reaction.

26. Process according to claim 19, wherein the distilling is carried out at a temperature between 100° C. and 160° C., in a distillation column having from 5 to 15 theoretical trays.

* * * * *